US008673112B2

(12) United States Patent
Nilsen et al.

(10) Patent No.: US 8,673,112 B2
(45) Date of Patent: Mar. 18, 2014

(54) METHOD AND DEVICE FOR THERMAL HYDROLYSIS AND STEAM EXPLOSION OF BIOMASS

(75) Inventors: Pål Jahre Nilsen, Bødalen (NO); Odd Egil Solheim, Hvalstad (NO); Paul Walley, Staffs (GB)

(73) Assignee: Cambi Technology AS, Asker (NO)

( * ) Notice: Subject to any disclaimer, the term of this patent is extended or adjusted under 35 U.S.C. 154(b) by 0 days.

(21) Appl. No.: 13/383,452

(22) PCT Filed: Jul. 12, 2010

(86) PCT No.: PCT/EP2010/059952
§ 371 (c)(1),
(2), (4) Date: Jan. 11, 2012

(87) PCT Pub. No.: WO2011/006854
PCT Pub. Date: Jan. 20, 2011

(65) Prior Publication Data
US 2012/0111515 A1    May 10, 2012

(30) Foreign Application Priority Data

Jul. 13, 2009    (NO) .................................. 2009 2647

(51) Int. Cl.
*D21C 3/26*        (2006.01)
*D21C 7/08*        (2006.01)
*B01J 3/00*        (2006.01)
*D21C 1/02*        (2006.01)
*B01J 3/02*        (2006.01)

(52) U.S. Cl.
CPC .. *D21C 3/26* (2013.01); *D21C 7/08* (2013.01); *B01J 3/02* (2013.01); *B01J 3/006* (2013.01); *D21C 1/02* (2013.01)
USPC .................. 162/21; 162/68; 162/46; 162/47; 162/239; 162/247; 422/185; 422/608

(58) Field of Classification Search
USPC ........... 162/21, 22, 68, 239, 246, 247, 46, 47; 422/185, 608, 307–309
See application file for complete search history.

(56) References Cited

U.S. PATENT DOCUMENTS 4,017,421  A        4/1977  Othmer
4,138,311  A  *     2/1979  Neno .............................. 162/28
(Continued)

FOREIGN PATENT DOCUMENTS

DE         10117321 A1    4/2002
NO           300094 B1    4/1997
(Continued)

OTHER PUBLICATIONS

Galiana Lopez, Paula, "International Search Report" for PCT/EP2010/059952, as mailed Sep. 28, 2010, 4 pages.

*Primary Examiner* — Eric Hug
(74) *Attorney, Agent, or Firm* — Winstead PC

(57) ABSTRACT

It is described a process for thermal hydrolysis and team explosion of biomass, said method comprising the steps of: (i) leading the biomass approximately continuous to a first preheating step and preheat the biomass, (ii) leading the preheated biomass into at least two reactors sequentially, (iii) heating and pressurising the reactor by addition of steam, (iv) keeping the reactor(s) at a certain temperature and pressure for a certain time, (v) leading the heated and pressurized biomass from the reactor(s) to a first pressure relief tank without any substantial pressure reduction and quickly relief the pressure of the biomass by means of a nozzle, in order to disintegrate the biomass, (vi) leading the biomass from the first pressure relief tank to a second pressure relief tank having a lower pressure than the pressure of the first pressure relief tank, (vii) leading the so treated biomass to a downstream facility for subsequent treatment. The invention also comprises a device for thermal treatment of biomass.

14 Claims, 2 Drawing Sheets

(56) References Cited

U.S. PATENT DOCUMENTS

| | | | |
|---|---|---|---|
| 4,163,687 A * | 8/1979 | Mamers et al. | 162/21 |
| 4,261,836 A | 4/1981 | Koglin | |
| 6,966,989 B2 | 11/2005 | Hojsgaard et al. | |
| 2004/0060863 A1 | 4/2004 | Hojsqaard et al. | |

FOREIGN PATENT DOCUMENTS

| | | |
|---|---|---|
| NO | 310717 B1 | 8/2001 |
| NO | 324955 B1 | 1/2008 |
| WO | WO-96/09882 A1 | 4/1996 |
| WO | WO-0073221 A1 | 12/2000 |
| WO | WO-2008/026932 A1 | 3/2008 |

* cited by examiner

METHOD AND DEVICE FOR THERMAL HYDROLYSIS AND STEAM EXPLOSION OF BIOMASS

The present invention relates to a method for thermal hydrolysis and steam explosion of biomass. Furthermore, the invention encompasses a device for thermal hydrolysis of biomass, said device encompasses a preheating tank for preheating of the biomass to a desired temperature, one or more reactors connected to the preheating tank and one or more pressure relief tanks connected to the reactor(s) for relief of the pressure on the biomass.

Special nozzles are used in the pressure relief tank that give a rapid and strong drop in pressure and improved disintegration of the cell structures of the biomass. The new system opens for a faster cycle time and more optimal filling of the reactor volume. The method and device optimise the use of energy by using one or two pressure relief tanks, where the latter operates at an underpressure.

BACKGROUND

Thermal hydrolysis and steam explosion is a known method to break down biomass so that it is better suited to anaerobic degradation. There are several patented methods that describe both batch wise and continuous processes. Batch wise treatment of biomass leads to both approved sterilisation and infection prevention by ensuring the necessary residence time at high temperatures. This is different to continuous processes that can not document that all the biomass has been at the right temperature for sufficient time. There are, in particular, two methods for batch wise thermal hydrolysis that are known.

WO96/09882 (Solheim et al) describes an energy efficient process where the biomass is preheated in a preheating tank with the help of steam returned from a downstream process before it is pumped into one of several parallel reactors. The biomass is supplied new steam for heating and is held at the predetermined temperature and pressure for the required time. Thereafter, the reactor is relieved and steam is led back to the reheating tank for energy recovery. When the reactor pressure has sunk to a desired level (typically 2-4 bara) the steam return from the reactor to the preheating tank is shut. The biomass is thereafter blown over to a pressure relief tank at a low pressure (typically 1.2 bara). The advantage of this system is that with a relatively low pressure in the pressure relief tank one can recover a large fraction of the energy from the reactor after completed thermal hydrolysis. The pressure reduction in the reactor before it is blown to the pressure relief tank is described as necessary to reduce the erosion problems in the pipe system between the reactor and the pressure relief tank.

U.S. Pat. No. 6,966,989 (Højsgaard et al) does not use, like WO96/09882, a preheating tank but has parallel reactors that also function as preheating tanks. This is achieved in that one reactor at a high pressure is relieved by letting steam over to a waiting reactor at low pressure. When these reactors are at the same pressure, the steam transfer is stopped and the hydrolysed biomass in the reactor is blown over to a low pressure pressure relief tank. Energy recovery from the pressure relief tank is not described. By filling a reactor with steam from another reactor one does not come down very far in pressure and the energy recovery is thereby not optimal.

Common for these two systems is a limited possibility to blow the biomass from the reactor to the pressure relief tank at high pressure. They have both a controlled pressure relief of the steam phase from the reactor before the biomass is blown over into a pressure relief tank. This occurs at a considerably lower pressure than the hydrolysis pressure.

An element that makes the two systems more expensive is that the reactors must have both a steam line with a control valve on top and a liquid/slurry line with a shut-off valve in the bottom of the reactor.

Furthermore, a method and device is known from WO0073221 (Solheim et al) for continuous hydrolysis of the biomass/sludge. The biomass is preheated in a tank with spent steam from the pressure relief tank of the process. The heated sludge is fed via a feeding pump and a mixing unit to a reactor. The pressure to the sludge is increased before this is fed into the reactor. In the reactor the temperature and pressure are controlled and fresh steam can be supplied to the reactor. The heated and pressurised biomass is then fed into a pressure relief tank which is fitted with a nozzle for the relief of the pressure. In this tank, a sudden reduction of the pressure occurs, a so-called steam explosion. Steam from the pressure relief tank can be returned to the preheating unit.

A method for thermal hydrolysis of lignocellulose is known from WO 2008026932 (Solheim et al). The lignocellulose is hydrolysed with the use of two reactors, whereupon these are supplied steam for heating and pressurising. The reactors can operate sequentially before the mass is fed in to a flash tank, where, because of the pressure difference between them, a steam explosion of the mass occurs.

Another limitation with the prior processes is the time it takes for the pressure relief of the tank before one blows the biomass to the pressure relief tank. It takes time to boil off the steam for the pressure relief. This is described in U.S. Pat. No. 6,966,989 with a typical cycle time of 100-360 minutes, with a preferred cycle time of 150-160 minutes with the use of three reactors.

Since the steam shall exit at the top of the reactor without the biomass following, the reactor must have a considerable steam volume above the liquid phase to avoid foaming and liquid being dragged out in the steam return line. This limits the active volume of the reactor. A further limitation is the need for a large liquid surface to prevent shock boiling. This results in a need for a large diameter/height ratio in the reactor, which is not optimal for a pressure tank.

Steam explosion of biomass at large pressure drops over a short time will give greater cell destruction and larger bioavailability of the biomass. This will lead to a higher production of biogas in a downstream, anaerobic degradation tank. Therefore, it is desirable with the fastest possible and the biggest possible pressure drop when the biomass is blown over into the pressure relief tank.

The system according to the present invention protects the possibility of blowing the biomass at hydrolysis pressure, the highest in the process. This is done by using an especially robust nozzle at the end of the blow pipe between the reactor and the pressure relief tank which takes nearly the whole of the drop in pressure. Thereby the largest possible steam explosion and cell destruction in the biomass are ensured. The nozzle consists of an erosion resistant material, preferably a ceramic material, and is formed so that the biomass is blown down onto the liquid surface in the pressure relief tank. The erosion is thereby reduced to a minimum. The velocity upstream of the nozzle is low and ordinary pipe parts can thereby be used in the blow pipe between the reactor and the pressure relief tank.

As one blows at the hydrolysis pressure and has no pressure relief of steam at the top of the reactor, one can fill the reactors nearly to the top. The only limitation is to have sufficient volume for the condensing steam which is used for the heating (typically about 10% extra volume).

The reactors in the system according to the present invention can be manufactured to be long and slim, as there are no requirements to the surface area of the liquid phase because no steam is to be boiled off for pressure relief. This is cost effective with regard to use of materials and means a reduced need for floor area.

The system and the method according to the present invention optimise the cycle time to utilise the reactor volume optimally. Normally the requirement for sterilisation will be to keep the biomass at 133° C. for at least 20 minutes. When the system comprises, for example, three reactors, filling for 15 minutes, holding for 20 minutes and emptying for 15 minutes will lead to a constant consumption of steam while the requirement for sterilisation is met. This cycle time of 45 minutes means a considerably increased capacity compared to, for example, the system according to U.S. Pat. No. 6,966,989. If there is no requirement for sterilisation, the holding time and the temperature can be different from those given above. An embodiment of the system according to the present invention with three reactors can, with this cycle time, fill and empty four reactors per hour (see FIG. 2).

The system according to the present invention encompasses at least two pressure relief tanks in series to recover more energy. The second pressure relief tank is under vacuum so that steam boils off at lower temperature (for example, 0.7 bar gives 90° C.). This results in a typically 20% better energy efficiency than the system according to WO96/09882.

By controlling the flow of energy to the reactor and/or preheating tank, respectively, one can exactly achieve the desired pressure and temperature in the preheating tank. This results in a flexible system with good process control. With this control one is flexible with regard to further preheating of the biomass even before it gets to the preheating tank. By leading more of the energy to the reactor, one can permit preheating of the sludge with low temperature energy.

By using two pressure relief tanks the pressure in the first can be higher than that described in Solheim et al without affecting the total energy recovery. This can be advantageous because the preheating tank will thereby reach a higher pressure. All non-condensing gases in the process (foul gas) end up in the preheating tank. These gases often smell badly and ought to be transported in a closed system to the decomposition tank for biological degradation. If the pressure in the preheating tank is low, it may be necessary with a system that compresses the non-condensing gases to transport them into the degradation tank. With the present invention one eliminates the need for such a system.

Neither WO96/09882 nor U.S. Pat. No. 6,966,989 describe handling of the non-condensing gases. In the system according to U.S. Pat. No. 6,966,989 these gases can be accumulated in the reactor as flash steam only goes between the reactors. This represents a considerable problem as the pressure and the temperature will thereby no longer follow the saturation curve for water/steam. The pressure in the reactors can rise to a nominally correct level without the necessary hydrolysis temperature being reached.

A possible way to eliminate accumulation of non-condensing gases is to ensure that the reactor is emptied completely for the liquid phase and thereafter also empty the steam phase from the reactor to the pressure relief tank. This is time consuming and reduces the capacity of the system. The present invention solves this problem by leading the small amounts of non-condensing gases from the reactor to the preheating tank in a small gas return line. This line is opened a short period during the filling of the reactor with biomass.

An important feature that distinguishes the present invention from what is known from WO0073221 is that the method according to the present invention is a batch process while the method according to WO0073221 is a continuous process. Correspondingly, the methods according to WO96/09882 and WO2008026932 are also batch processes. The main feature of the present invention is not direct steam supply to the reactor, but the fact that with the help of a nozzle one can treat sludge that contains erosive particles. This is not possible with the method according to WO0073221 as this uses a pump to pressurise the sludge in the reactor. Neither WO96/09882 nor WO2008026932 comprise a nozzle and must therefore pressure relieve the reactor before the sludge can be transferred to the pressure relief tank. Thereby, the present invention solves the problems which WO96/09882 and WO2008026932 have not solved.

The aim of the present invention is to provide a system and a method with which the above mentioned disadvantages of the previously known solutions are eliminated or much reduced.

This is achieved with a method for thermal hydrolysis and steam explosion of biomass, said method encompasses the following steps:

(i) Feeding the biomass approximately continuously into a first preheating step and heating the biomass,
(ii) leading the preheated biomass sequentially into at least two reactors,
(iii) heating and pressurising the reactor by the supply of steam,
(iv) holding the reactor(s) at a given temperature and pressure over a given time,
(v) leading the heated and pressurised biomass from the reactor(s) to a first pressure relief tank without any substantial reduction in pressure and relieving the pressure of the biomass quickly with the help of a nozzle so that the biomass is broken up,
(vi) leading the biomass from the first pressure relief tank to a second pressure relief tank at a lower pressure than the pressure in the first pressure relief tank,
(vii) leading the treated biomass to a downstream installation for further treatment.

The pressure reduction in step (v) is preferably in the area 2-13 bar and the pressure reduction in step (vi) is preferably in the area 0.4-1.6 bar.

The pressure in the reactor is preferably of the order of 4-14 bar abs.

The pressure in the first pressure relief tank is preferably of the order of 1.2-2 bar abs.

The pressure in the second pressure relief tank is preferably of the order of 0.3-0.8 bar abs.

The number of sequential reactors is preferably three and step (ii) has a duration of about 15 minutes, step (iv) has a duration of preferably about 20 minutes and step (v) has a duration of preferably about 10 minutes.

The method is further characterised by stopping the filling of the first reactor and immediately starting the filling of the second reactor and when the second reactor is filled, starting the filling of the third reactor and repeating this sequence continuously.

Steam from the first pressure relief tank is led to the preheating tank to heat this.

Steam from the second pressure relief tank is led to the preheating tank and/or the reactor for the heating of these.

Non-condensing gases are led back from the reactor to the preheating tank and thereafter the non-condensing gases are led from the preheating tank to a subsequent treatment step.

The invention also relates to a device for thermal hydrolysis of organic material, said device encompasses a preheating tank for preheating of the biomass to a desired temperature, one or more reactors connected with the preheating tank and one or more pressure relief tanks connected with the reactor(s) for relief of the pressure from the biomass, said device is characterised in that it comprises a steam supply line that supplies steam from a steam supply source to the, at least, two reactors, a line that leads pressurised biomass from the reactor(s) to a nozzle in the first pressure relief tank without any substantial pressure reduction for relief of the pressure of the biomass from the reactor and a line for supply of steam from the one pressure relief tank to the preheating tank, and a second pressure relief tank connected with the first pressure relief tank for relief of the pressure of the biomass from the first pressure relief tank, said second pressure relief tank being connected with the preheating tank with a line for return of steam from the second pressure relief tank to the preheating tank.

The preheating tank is preferably connected with an agitation pump cycle for recirculation of preheated biomass, that the steam return line from the second pressure relief tank is connected with an agitation pump cycle via an ejector and/or that the steam return line from the second pressure relief tank is connected via an ejector with the steam supply line for supply of steam to the reactor(s).

The steam return line from the second pressure relief tank can possibly be connected with one or more compressors to compress the steam from the second pressure relief tank and lead the compressed steam to the preheating tank and/or the reactor(s).

The, at least, one reactor is connected to the preheating tank with a line for non-condensing gases and the preheating tank comprises a line to lead the non-condensing gases to a downstream treatment installation.

The first pressure relief tank preferably comprises one or more nozzles for the supply of hydrolysed biomass from the, at least, one reactor to achieve maximum pressure relief and disintegration of the biomass.

SHORT DESCRIPTION OF THE DRAWINGS

DETAILED DESCRIPTION OF PREFERRED EMBODIMENTS

Figure 1:
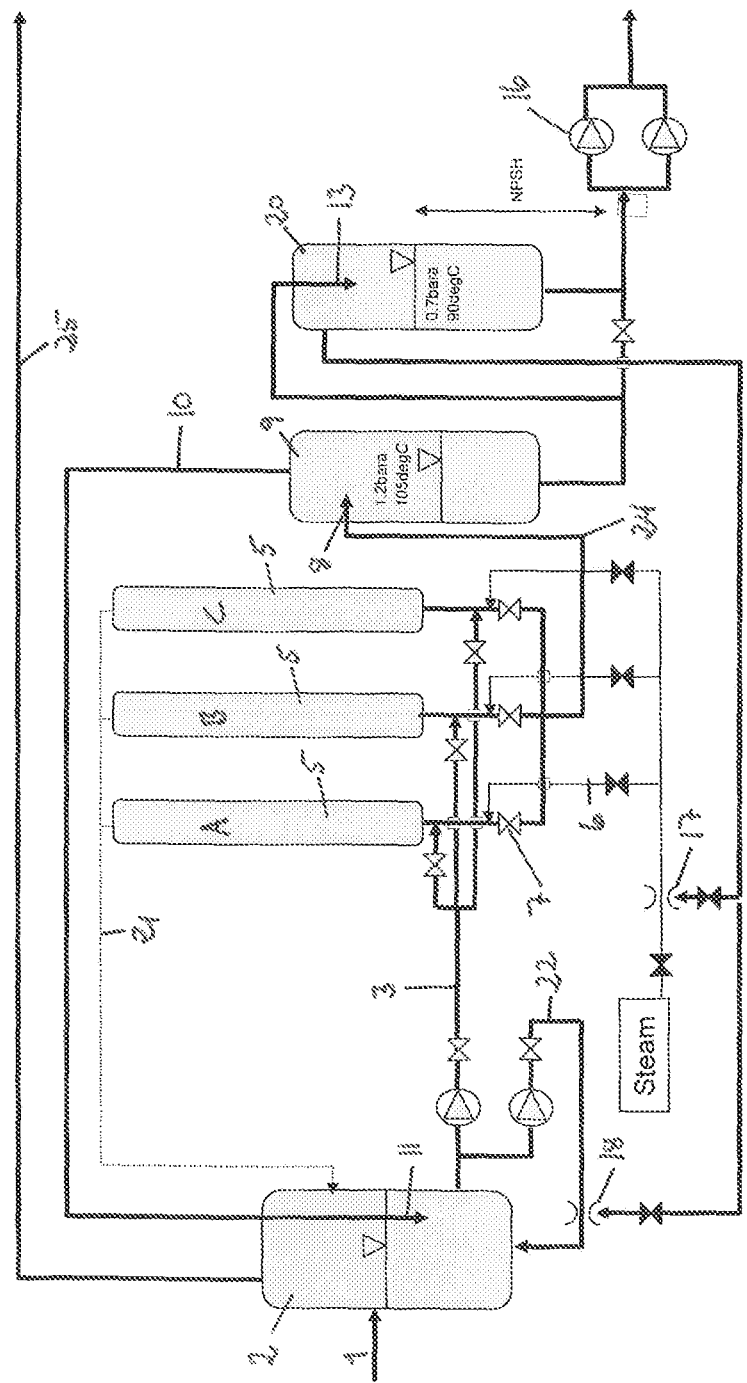
FIG. 1 shows schematically an embodiment of the system according to the present invention.

As shown schematically in FIG. 1, the biomass with a typical dry matter content of 5-30% (1) is pumped into a preheating tank 2 and preheated by return steam (10, 23) from a first pressure relief tank 9 and a second pressure relief tank 20. The biomass is thereafter pumped via a line 3 to the reactor 5. Steam is supplied to the reactor 5 during and after the filling of the biomass to heat this up to a desired temperature. The pressure in the reactor 5 becomes equal to the saturation pressure of water at the same temperature. After the desired processing time the bottom valve 7 in the reactor 5 is opened and the hydrolysed biomass is blown over into the first pressure relief tank 9 via a line 24. At the end of the line 24 between the reactor 5 and the first pressure relief tank 9 is a robust nozzle 8 that takes most of the pressure drop from the reactor pressure (typically 4-14 bar abs) to the pressure of the first pressure relief tank 9 (typically 1.2-2 bar abs). Thereby a very fast and powerful expansion of the steam is ensured, which leads to a very effective disintegration of the cell structures of the biomass.

Flash steam from the first pressure relief tank 9 is led to the liquid phase in the preheating tank 2 via a steam line 10 and a steam nozzle 11 for energy recovery. The steam nozzle 11 ensures good mixing of the steam and the liquid for energy recovery to the liquid. Thereby, the pressure in the preheating tank 2 balances with the pressure in the first pressure relief tank 9. Biomass from the first pressure relief tank 9 flows on into a second pressure relief tank 20 via a nozzle 13 that ensures small droplets and a large surface area for maximum pressure relief and, in addition, cooling of the biomass. The flash steam from the second pressure relief tank 20 is led to the reactor 5 and/or the preheating tank 2 for energy recovery. Low pressure is maintained in the second pressure relief tank 20 (underpressure) with the help of steam ejectors that ensure the necessary suction pressure. A steam driven ejector 17 compresses some of the steam from the second pressure relief tank 20 and leads this into the reactor 5. The need for fresh steam to the reactor 5 is thereby reduced with a corresponding amount. A liquid driven ejector 18 is connected to the pump agitation 22 of the preheating tank 2 and compresses the rest of the steam from the second pressure relief tank 20 and leads this to the preheating tank 2 for energy recovery. The liquid driven ejector can possibly be placed in the line 3 that leads the biomass to the reactors. This will make possible further heating of the biomass in the reactor. The biomass from the second pressure relief tank 20 can, for example, be pumped to a subsequent degradation tank (not shown). As the second pressure relief tank 20 has an underpressure, an elevation of the liquid surface is required in the second pressure relief tank 20 to ensure sufficient suction pressure on the pumps 16 that deliver the biomass further on to a subsequent degradation tank (not shown).

According to another embodiment of the present invention there is only one pressure relief tank 9.

A return line 21 for non-condensing gases is also shown in FIG. 1. Non-condensing gases from the reactors 5 are returned to the preheating tank 2. From the preheating tank 2 the non-condensing gases are led in a line 25 to a downstream digester.

In the embodiment of the present invention shown in FIG. 1 three reactors 5 coupled in parallel are provided. The number of reactors can, of course, be different from this. With the three reactors one can achieve a continuous filling of the reactors.

Figure 2:
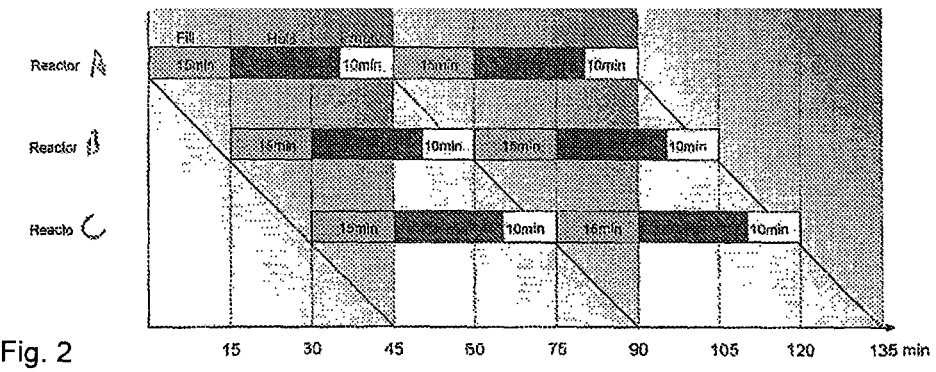
FIG. 2 is a process diagram that shows examples of cycle times for the different operations of the system and the method according to the present invention.

FIG. 2 shows schematically an example of how the cycle for filling, holding and emptying of the three reactors are phase displaced to ensure constant consumption of steam, short cycle time and the most even steam return possible from the pressure relief tank to the preheating tank. A first reactor 5A is filled with preheated biomass from the preheating tank 2 and steam is supplied until the desired pressure and temperature have been reached. Thereafter, the biomass is held in the reactor 5A while reactor 5B is being filled. As soon as reactor 5B is filled, the filling of reactor 5C commences. After the desired holding time in reactor 5A, the valve 7 at the bottom of the reactor 5A is opened and the biomass is led over into the pressure relief tank 9, where a very rapid pressure relief occurs which tears up the cell structure of the hydrolysed biomass. After reactor 5 has been emptied, the filling of reactor 5C stops and the filling of reactor 5A starts up again, at the same time as the supply of biomass from the preheating tank to the reactor 5C is stopped. This cycle is repeated continuously.

With this method an approximately continuous transfer of biomass from the preheating tank 2 to the reactors 5 occurs.

Figure 3:
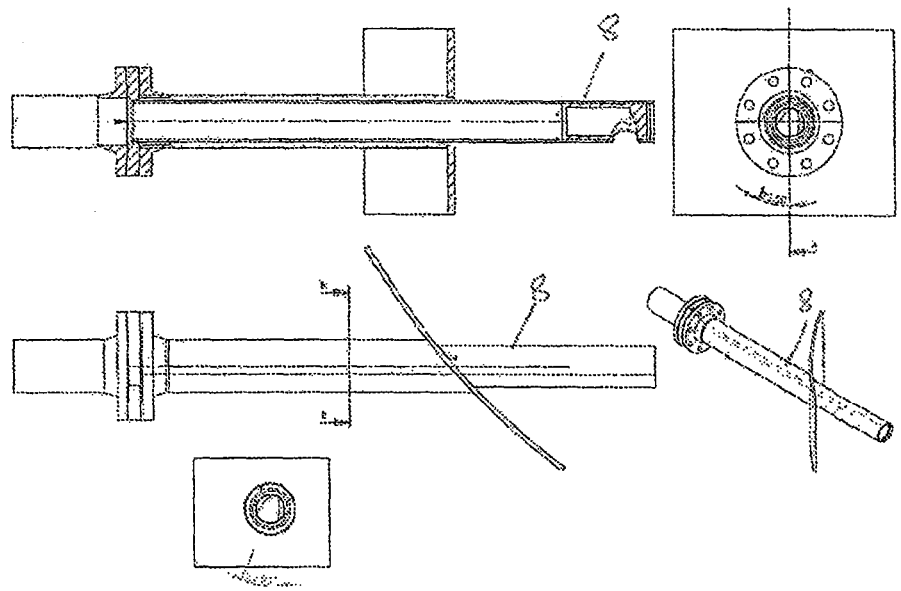
FIG. 3 shows an embodiment of a nozzle that can be used in the system according to the present invention.

FIG. 3 shows a typical shape of the nozzle in the first pressure relief tank, that ensures maximum steam explosion and disintegration of the biomass. It is feasible to use more than one nozzle in the pressure relief tank. The nozzle is described in more detail in our patent application submitted at the same time as the present application.

Even if steam return via ejectors is described here, it is also possible to collect low pressure steam from the second pressure relief tank 20 by other methods, such as liquid ring compressors or gas compressors.

The invention claimed is:

1. A method for thermal hydrolysis and steam explosion of biomass, the method comprising:
    feeding the biomass approximately continuously into a first preheating tank and heating the biomass;
    leading the preheated biomass sequentially into at least two reactors;
    heating and pressurising the reactor by a supply of steam;
    holding the reactor(s) at a given temperature and pressure over a given time;
    leading the heated and pressurised biomass from the reactor(s) to a first pressure relief tank without any substantial reduction of the reactor pressure;
    relieving the pressure in the biomass quickly via a nozzle so that the biomass is broken up in the first pressure relief tank;
    leading the biomass from the first pressure relief tank to a second pressure relief tank at a lower pressure than the pressure in the first pressure relief tank;
    applying a vacuum to the second pressure relief tank such that the pressure in the second pressure relief tank is on the order of approximately 0.3-approximately 0.8 bar abs;
    leading steam from the second pressure relief tank to at least one of the first preheating tank and a reactor of the at least two reactors for heating; and
    leading the biomass to a downstream installation for further treatment.

2. The method according to claim 1, wherein the relieving the pressure is in the range of approximately 2-13 bar and the applying the vacuum is in the range of approximately 0.3 to approximately 0.8 bar.

3. The method according to claim 1, wherein a pressure in a reactor of the at least two reactors is on the order of approximately 4-14 bar.

4. The method according to claim 1, wherein a pressure in the first pressure relief tank is on the order of approximately 1.2-2 bar abs.

5. The method according to claim 1, wherein the at least two reactors comprises three reactors;
    the leading the preheated biomass has a duration of about 15 minutes;
    the holding the reactor has a duration of about 20 minutes; and
    the leading the heated and pressurized biomass has a duration of about 10 minutes.

6. The method according to claim 5, wherein:
    when filling of a first reactor of the at least two reactors is stopped, filling of a second reactor commences immediately; and
    when the second reactor is full, filling of a third reactor of the at least two reactors starts and this sequence is continuously repeated.

7. The method according to claim 1, wherein steam is led from the first pressure relief tank to the preheating tank for heating of this.

8. The method according to claim 1, wherein:
    non-condensing gases are led from a reactor of the at least two reactors to the preheating tank and thereafter the non-condensing gases are led from the preheating tank to a subsequent treatment step.

9. A device for thermal hydrolysis of biomass, the device comprising:
    a preheating tank for preheating of biomass to a desired temperature;
    two or more reactors connected to the preheating tank;
    one or more pressure relief tanks connected to the reactor(s) for relief of pressure on the biomass;
    a steam supply line that supplies steam from a steam supply source to the at least two reactors;
    a line that leads pressurised biomass from the two or more reactors to a nozzle in a first pressure relief tank without essential pressure reduction for relief of pressure on the biomass from the reactor;
    a steam return line for supply of steam from the first pressure relief tank to the preheating tank; and
    a second pressure relief tank connected to the first pressure relief tank for relief of pressure on the biomass from the first pressure relief tank, the second pressure relief tank has a vacuum applied thereto and is connected to the preheating tank with a line for return of steam from the second pressure relief tank to at least one of the preheating tank and the two or more reactors.

10. The device according to claim 9, wherein the preheating tank is connected to an agitation pump cycle for recirculation of preheated biomass, that at least one of the steam return line from the second pressure relief tank is connected to the agitation pump cycle via an ejector.

11. The device according to claim 9, wherein the steam return line from the second pressure relief tank is connected to one or more compressors for compression of steam from the second pressure relief tank, wherein the steam return line leads the compressed steam to at least one of the preheating tank and the two or more reactors.

12. The device according to claim 9, wherein two or more reactors are connected to the preheating tank with a line for non-condensing gases and that the preheating tank encompasses a line to lead the non-condensing gases to a downstream treatment installation.

13. The device according to claim 9, wherein the first pressure relief tank comprises one or more nozzles for supplying hydrolysed biomass from at least one reactor of the two or more reactors to achieve maximum pressure relief and disintegration of the biomass.

14. The device according to claim 9, wherein the steam return line from the second pressure relief tank is connected via an ejector with the steam supply line for supply of steam to the two or more reactors.

* * * * *

UNITED STATES PATENT AND TRADEMARK OFFICE
CERTIFICATE OF CORRECTION

| | |
|---|---|
| PATENT NO. | : 8,673,112 B2 |
| APPLICATION NO. | : 13/383452 |
| DATED | : March 18, 2014 |
| INVENTOR(S) | : Pål Jahre Nilsen et al. |

It is certified that error appears in the above-identified patent and that said Letters Patent is hereby corrected as shown below:

In the Claims:

Column 8, Claim 7    Replace "tank for heating of this"
With -- tank for heating. --

Signed and Sealed this
Sixteenth Day of September, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,673,112 B2 | Page 1 of 1 |
| APPLICATION NO. | : 13/383452 | |
| DATED | : March 18, 2014 | |
| INVENTOR(S) | : Pål Jahre Nilsen et al. | |

It is certified that error appears in the above-identified patent and that said Letters Patent is hereby corrected as shown below:

In the Claims:

Column 8, Lines 5-6, Claim 7     Replace "tank for heating of this"
                                 With -- tank for heating. --

This certificate supersedes the Certificate of Correction issued September 16, 2014.

Signed and Sealed this
Fourteenth Day of October, 2014

Michelle K. Lee
*Deputy Director of the United States Patent and Trademark Office*